US00PP24021P3

(12) United States Plant Patent
Blom

(10) Patent No.: US PP24,021 P3
(45) Date of Patent: Nov. 5, 2013

(54) ***CHRYSANTHEMUM* PLANT NAMED 'ZANMUAVAL RED'**

(50) Latin Name: ***Chrysanthemum×morifolium* Ramat.**
Varietal Denomination: Zanmuaval Red

(75) Inventor: Wilhelmus Bernardus Blom, Leimuiden (NL)

(73) Assignee: Chrysanthemum Breeders Association Research B.V., Aalsmeer (NL)

( * ) Notice: Subject to any disclaimer, the term of this patent is extended or adjusted under 35 U.S.C. 154(b) by 87 days.

(21) Appl. No.: 13/385,346

(22) Filed: Feb. 15, 2012

(65) Prior Publication Data

US 2013/0212761 P1 Aug. 15, 2013

(51) Int. Cl.
*A01H 5/00* (2006.01)

(52) U.S. Cl.
USPC ..... Plt./298

(58) Field of Classification Search
USPC ..... Plt./298
See application file for complete search history.

*Primary Examiner* — Annette Para

(74) *Attorney, Agent, or Firm* — Steptoe & Johnson LLP

(57) ABSTRACT

A *Chrysanthemum* plant named 'Zanmuaval Red' characterized by its medium sized blooms with dark red ray florets and prolific branching; natural season flower date datum; blooming for a period of five weeks.

3 Drawing Sheets

Botanical designation: *Chrysanthemum×morifolium* Ramat.

Cultivar denomination: 'Zanmuaval Red'.

RELATED CULTIVARS

The new plant is a mutant obtained from the *Chrysanthemum* plant 'Zanmuaval' (U.S. Plant Pat. No. 22,659).

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuaval Red'. The new plant is a product of a breeding and selection program which had the objective of finding color mutants from existing parent plants. The new plant comprises a whole plant mutant of the *Chrysanthemum* plant named 'Zanmuaval'. Plants from the new cultivar 'Zanmuaval Red' differ from plants of the parent in the color of their ray-florets; those of the new plant 'Zanmuaval Red' are dark red, while those of the parent are purple.

The new cultivar was discovered as a color mutant in April 2009 by Wilhelmus Bernardus Blom in a controlled environment (greenhouse) in Rijsenhout, The Netherlands. The first act of asexual reproduction of 'Zanmuaval Red' was accomplished when after planting of the mutant as a motherplant in May 2009, vegetative cuttings from this mutant were taken and propagated further in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
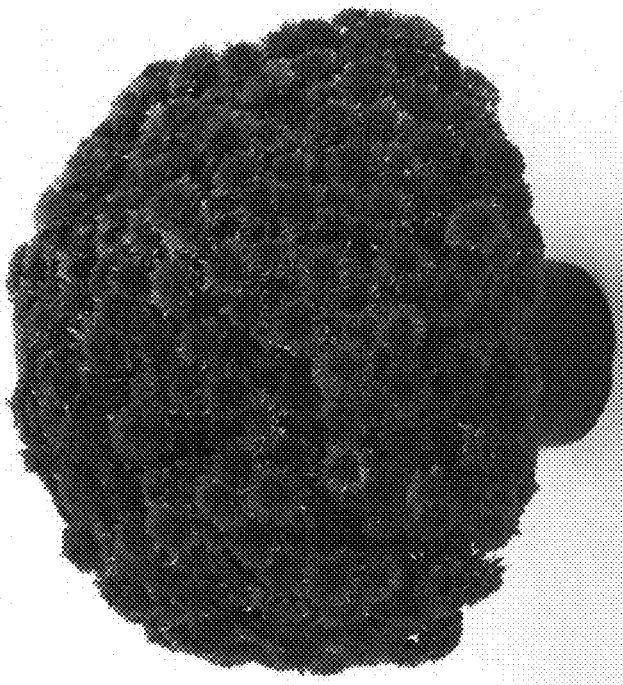
FIG. 1 shows a plant of the cultivar in full bloom.
Figure 2:
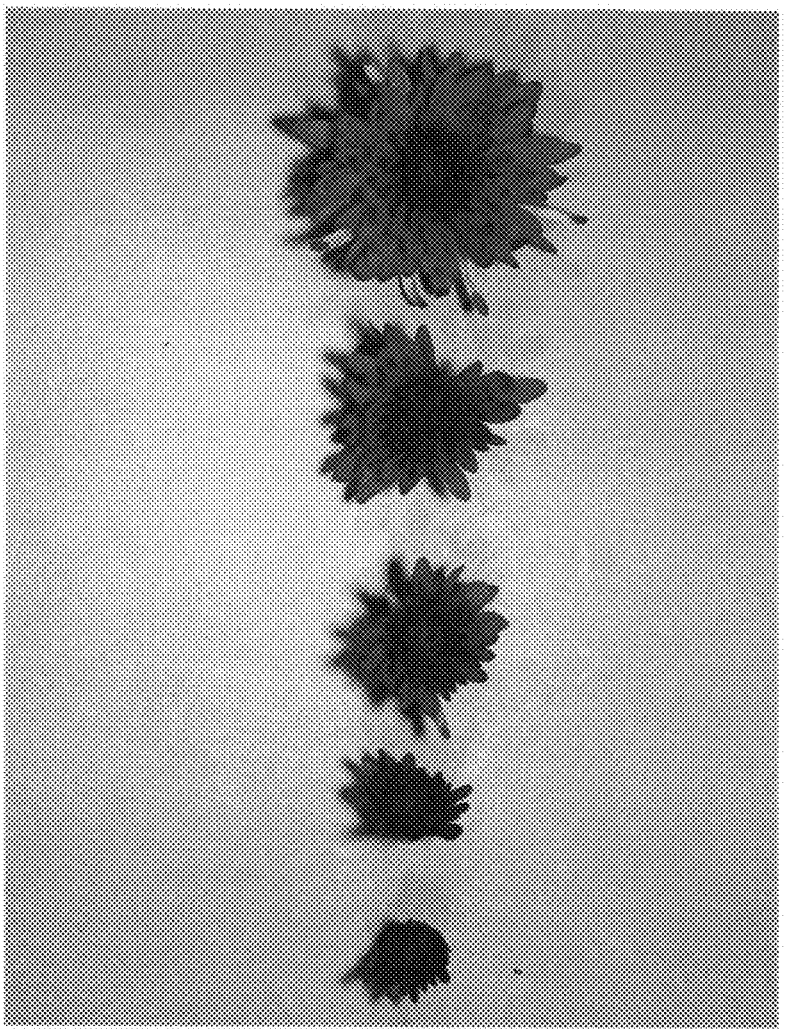
FIG. 2 shows the various stages of blooms of the new cultivar.
Figure 3:
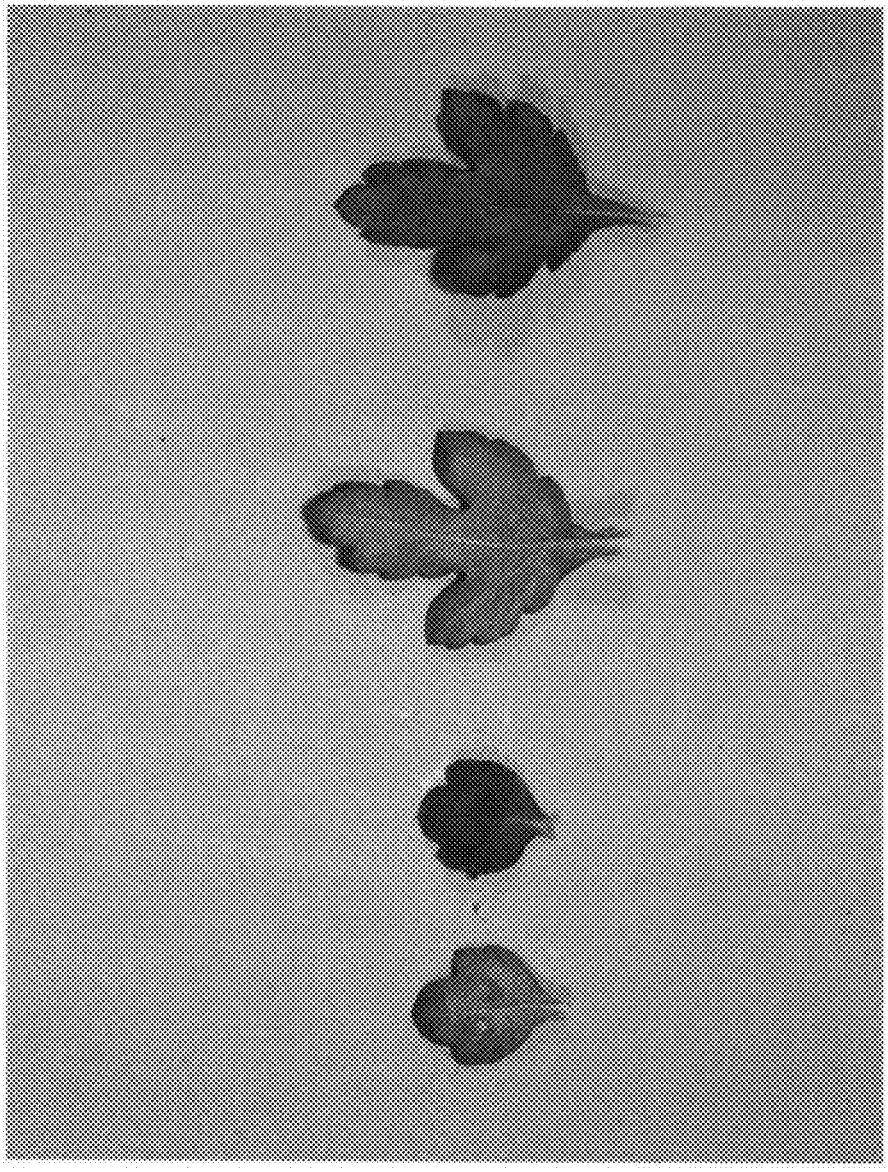
FIG. 3 shows the various stages of foliage of the new cultivar.

The observations and measurements were gathered from plants grown out door in Rijsenhout, The Netherlands, under natural day length and temperature and planted in week 22 in 2011. The natural blooming date of this crop was October 17 (week 42). The average height of the plants was 30 cm. No growth retardants were used. No tests were done on disease or insects resistance or susceptibility. No tests were done on cold or drought resistance. This new variety produces medium sized blooms with dark red ray florets blooming for a period of five weeks.

From the cultivars known to inventor the most similar existing cultivar in comparison to 'Zanmuaval Red' is 'Zanmuaval' (U.S. Plant Pat. No. 22,659), its parent plant, and 'Zanmuaval Orange' (U.S. Plant patent application Ser. No. 13/385,345), another mutant developed from the same parent plant. When 'Zanmuaval', 'Zanmuaval Orange' and 'Zanmuaval Red' are being compared the following differences in the color of the ray-florets are observed: that of 'Zanmuaval' is purple, while the color in 'Zanmuaval Orange' is bronze and in 'Zanmuaval Red' dark red.

The following is a description of the plant and characteristics that distinguish 'Zanmuaval Red' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

DETAILED BOTANICAL DESCRIPTION

Bud:

*Size*.—Small; cross-section 0.5 cm, height 0.3 cm.

*Shape*.—Oblate.

*Texture*.—Pubescent.
*Outside color*.—Greyed-green 191B.
Phyllaries:
*Number*.—20-22, arranged in 3 rows.
*Shape*.—Elliptic.
*Apex*.—Acute.
*Base*.—Truncate.
*Margin*.—Entire.
*Color*.—Upper surface: Greyed-green 191B. Lower surface: Green 138A.
*Length and width*.—1 cm; 0.1 cm.
*Texture*.—Pubescent.
Inflorescence:
*Type*.—Double.
*Height*.—1.5 cm.
*Diameter*.—5 cm.
*Peduncle length*.—5-6 cm.
*Peduncle color*.—Green 138C.
*Peduncle diameter*.—0.2 cm.
*Peduncle texture*.—Pubescent.
*Number per branch*.—Approx. 6 inflorescences.
*Duration of flowering*.—5 weeks.
*Seeds*.—Produced in small quantities, ovate, Greyed-brown 199A, length 1.5 mm, diameter 0.8 mm.
*Fragrance*.—Faint *Chrysanthemum* odor.
Color:
*Center of inflorescences*.—Immature stage: Greyed-Purple 183A. Mature stage: Greyed-Purple 183A.
*Color of upper surface of the ray-florets*.—Greyed-Purple 185B.
*Color of the lower surface of the ray-florets*.—Greyed-Red 182D.
*Tonality from distance*.—A garden mum with dark red flowers.
*Color of the ray-florets after aging of the plant*.—Greyed-Purple 185D.
Ray florets:
*Texture*.—Upper and lower surface smooth.
*Number*.—240-260.
*Shape*.—Elliptic.
*Type*.—Predominantly ligulate.
*Apex*.—Varying from acute to dentate.
*Base*.—Attenuate.
*Cross-section*.—Flat.
*Longitudinal axis of majority*.—Straight.
*Length of corolla tube*.—0.3-0.4 cm.
*Ray-floret margin*.—Entire.
*Ray-floret length*.—1.2-2.5 cm.
*Ray-floret width*.—0.2-0.5 cm.
*Ratio length/width*.—High.
Disc florets: Absent.
Receptacle:
*Color*.—Green 138C.
*Shape*.—Domed raised.
*Height*.—0.4 cm.
*Diameter*.—0.4 cm.
Reproductive organs:
*Androecium*.—Absent.
*Pollen*.—Not produced.
*Gynoecium*.—Present in ray-florets.
*Style length*.—3 mm.
*Stigma color*.—Yellow 7A.
*Stigma width*.—1 mm.
*Ovary*.—Enclosed in calyx.
Plant:
*Form*.—Grown as a spray type pot mum, outdoor raised and mounded.
*Growth habit*.—Spherical shape.
*Growth rate*.—Medium.
*Height*.—30 cm.
*Width*.—50 cm.
*Stem color*.—Greyed-brown 199A.
*Stem strength*.—Weak.
*Stem brittleness*.—Brittle.
*Stem anthocyanin coloration*.—Not observed.
*Internode length*.—2-4 cm.
*Length of lateral branch*.—From top to bottom 20 cm.
*Lateral branch color*.—Green 137 C.
*Lateral branch, attachment*.—Brittle.
*Lateral branch diameter*.—2 mm.
*Branching* (*average number of lateral branches*).—Prolific with 8-9 breaks after pinching.
*Natural season blooming date*.—October 17-21 (week 42).
Foliage:
*Leaf color*.—Upper side: Green 139A. Lower side: Green N138A.
*Color midvein*.—Upper side: Yellow-green 147D. Lower side: Yellow-green 148D.
*Size*.—Small.; length 3-5 cm, width 2-3.5 cm.
*Quantity* (*number per lateral branch*).—15-17.
*Shape*.—Elliptic.
*Texture upper side*.—Sparsely pubescent.
*Texture under side*.—Pubescent.
*Venation arrangement*.—Palmate.
*Shape of the margin*.—Serrated.
*Shape of base of sinus between lateral lobes*.—Rounded.
*Margin of sinus between lateral lobes*.—Diverging.
*Shape of base*.—Truncate.
*Apex*.—Mucronulate.
*Petiole length*.—0.3-0.8 cm.
*Petiole diameter*.—0.2-0.4 cm.
*Petiole color*.—Yellow-green 147D.

TABLE 1

| Differences with the comparison varieties | | | |
|---|---|---|---|
| | 'Zanmuaval Red' | 'Zanmuaval Orange' | 'Zanmuaval' |
| Color upper surface ray florets | Greyed-Purple 185B | Greyed-Orange 164B | Purple N79C |

I claim:

1. A new and distinct variety of *Chrysanthemum* plant as described and illustrated.

* * * * *